United States Patent [19]
Wolf

[11] Patent Number: 4,770,026
[45] Date of Patent: Sep. 13, 1988

[54] METHOD OF AND APPARATUS FOR TESTING BREATH ALCOHOL

[75] Inventor: Karl P. W. Wolf, St. Louis, Mo.

[73] Assignee: Alcotek, Inc., St. Louis, Mo.

[21] Appl. No.: 3,478

[22] Filed: Jan. 15, 1987

[51] Int. Cl.[4] .......................................... G01N 27/16
[52] U.S. Cl. ........................................ 73/23; 422/84; 436/900
[58] Field of Search ............. 73/23; 422/84; 436/900; 128/719, 730

[56] References Cited

U.S. PATENT DOCUMENTS

| | | | |
|---|---|---|---|
| 3,823,601 | 7/1974 | Hoppesch | 73/23 |
| 4,032,856 | 6/1977 | Goldner | 73/23 |
| 4,297,871 | 11/1981 | Wright et al. | 73/23 |
| 4,487,055 | 12/1984 | Wolf | 73/23 |

FOREIGN PATENT DOCUMENTS

1443438 7/1976 United Kingdom ..................... 73/23

Primary Examiner—Michael J. Tokar
Assistant Examiner—Joseph W. Roskos
Attorney, Agent, or Firm—Polster, Polster and Lucchesi

[57] ABSTRACT

Apparatus for measuring breath alcohol content by oxidizing breath alcohol in a fuel cell and utilizing substantially all of the electrons produced by said oxidation as a measure of the amount of alcohol contained in the sample. A working embodiment of the invention includes a resistor across terminals of the fuel cell with a resistance that is high enough to permit the voltage from the fuel cell to be accurately measured but low enough to permit the voltage to fall to a substantially steady minimum voltage within a time on the order of two minutes or less. The method of measuring breath alcohol concentration comprises integrating the entire area under the curve generated by the fuel cell output voltage between the beginning of oxidation of the alcohol in the fuel cell and the reaching of the substantially steady minimum.

4 Claims, 1 Drawing Sheet

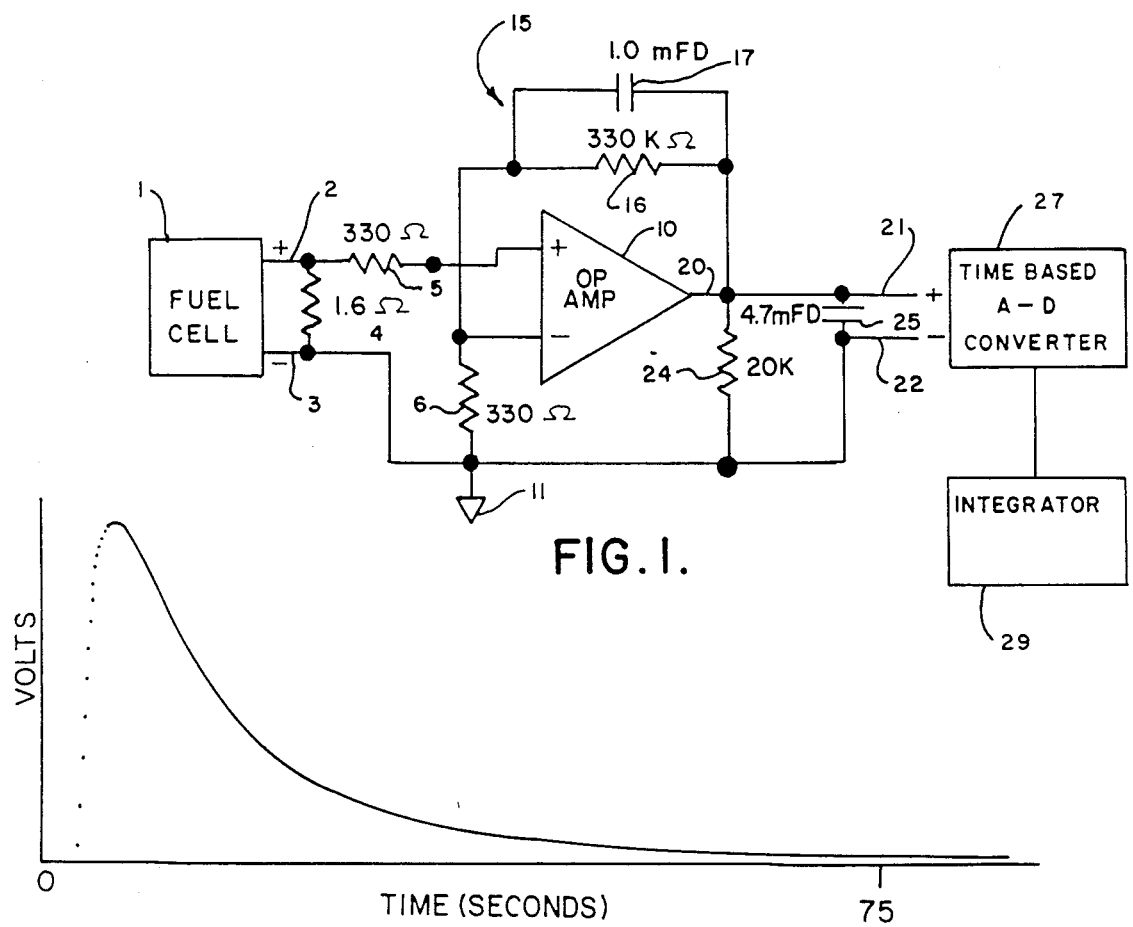
FIG. 1.
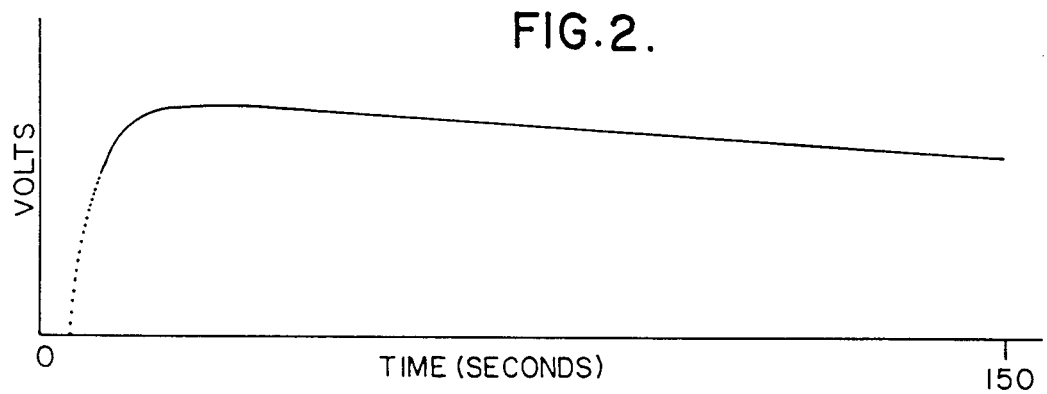
FIG. 2.
FIG. 3. PRIOR ART
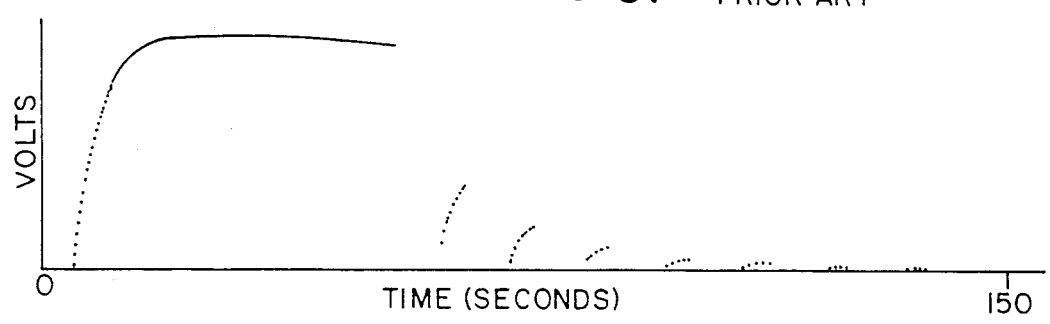
FIG. 4. PRIOR ART

METHOD OF AND APPARATUS FOR TESTING BREATH ALCOHOL

BACKGROUND OF THE INVENTION

The present invention has particular application to breath alcohol testing devices such as the ones sold by Intoximeters Inc., 1901 Locust Street, St. Louis, Mo., under the trademark ALCO-SENSOR, and especially to such devices equipped with fuel cells constructed as described in Wolf U.S. Pat. No. 4,487,055, but its use is not limited thereto.

In breath alcohol testing devices presently used commercially, in which fuel cells are employed, the conventional way of determining breath alcohol is to measure a peak voltage across a resistor due to the flow of electrons obtained from the oxidation of breath alcohol on the surface of the fuel cell. There are a number of problems. The peaks become lower with repeated use of the fuel cell. The peaks vary with different temperatures. In order to produce a high peak, it is customary to put across the output terminals of the fuel cell a high external resistance, on the order of a thousand ohms, but the use of such a high resistance produces a voltage curve which goes to the peak and remains on a high plateau for an unacceptably long time. To overcome that problem, present systems provide for shorting the terminals, which drops the voltage to zero while the short is across the terminals. However, it is still necessary to let the cell recover, because if the short is removed in less than one-half to two minutes after the initial peak time, for example, the voltage creeps up. Peak values for the same concentration of alcohol decline with repeated use whether the terminals are shorted or not, and require 15–25 hours to recover to their original values.

The individual fuel cells differ in their characteristics. All of them slump with repeated use in quick succession and also after a few hours' time of non-use. They degrade over time, and in the systems used heretofore, must be re-calibrated frequently. Eventually, they degrade to the place at which they must be replaced. Presently, the cell is replaced when it peaks too slowly or when the output at the peak declines beyond practical re-calibration, or when the background voltage begins creeping excessively after the short is removed from the cell terminals.

One of the objects of this invention is to provide apparatus and method that provide a measure of breath alcohol that is largely independent of the value of the peak voltage.

Another object is to provide such a device and method that require no recovery time beyond the period of measurement.

Other objects will become apparent to those skilled in the art in the light of the following description and accompanying drawing.

SUMMARY OF THE INVENTION

In accordance with this invention, generally stated, a method of measuring breath alcohol concentration is provided in which a breath sample is introduced to a fuel cell as it is in a conventional breath alcohol detector, wherein the number of electrons from the fuel cell resulting from oxidation of the alcohol in the breath rises to a peak and thereafter falls to a substantially steady minimum base to form a curve. In the present method, the entire area under the curve during the period between the beginning of oxidation and the reaching by the voltage of the substantially steady minimum, is integrated to provide a measure of substantially all of the electrons generated by the oxidation of the alcohol, and an intelligible signal representing that area is generated. The preferred method includes a step of establishing a base line output of the cell (if any) and electronically subtracting the area representing that output, over the measuring time during the oxidation process, from the area under the alcohol curve during that measuring period.

To permit the practice of the method, apparatus is provided in which an external resistor across the output terminals of the fuel cell has a resistance high enough to permit the voltage from the fuel cell to be accurately measured, but low enough to permit the voltage to fall to a substantially steady minimum voltage within a time on the order of 2 minutes maximum.

BRIEF DESCRIPTION OF THE DRAWINGS

In the drawings,

FIG. 1 is a circuit diagram showing one illustrative embodiment of circuit of this invention;

FIG. 2 is a graph showing the curve of voltage produced by the circuit of FIG. 1;

FIG. 3 is a graph showing the curve of voltage produced by conventional fuel cell breath alcohol testing equipment, unshorted through a period of 150 seconds; and FIG. 4 is a graph showing the voltage output from the fuel cell of the conventional breath tester shorted out after approximately one minute following the beginning of oxidation, illustrating the subsequent rise when the short is removed and replaced at about 5 second intervals following the initial shorting.

DESCRIPTION OF THE PREFERRED EMBODIMENT

Referring now to the drawing, and particularly to FIG. 1, for a circuit illustrating one embodiment of apparatus of this invention, reference numeral 1 indicates a fuel cell with output terminals 2 and 3. A resistor 4 is connected across the terminals 2 and 3. This resistor, which, in this embodiment, has a resistance of 1.6 ohms, is one method of implementing the present invention. In conventional breath testers, the value of this resistor is in the range of 300 to 1,000 ohms. Terminal 2 is connected, through a resistor 5, to the positive input of an operational amplifier (op amp) 10. The output terminal 3 is connected to a common or ground 11. The negative input of the op-amp is connected to ground 11 thru a resistor 6, in the illustration a 330 ohm resistor, and to the output terminal 20 of the op-amp thru a resistor 16, in the illustration a 330K ohm resistor, thus providing a negative feedback loop with a gain of approximately 1000 for slowly varying signals. The output terminal 20 is connected through a load resistor 24, to the common 11 and, by way of a conductor 21, to a time-based analog to digital converter 27. The A-D converter is electrically connected to an integrator 29 from which a display signal is derived.

As in the conventional circuit exemplified by the circuit shown in FIG. 1 of U.S. Pat. No. 4,487,055, the operational amplifier 10 is electrically connected to a battery or other power supply, not here shown. However, in the circuit shown in FIG. 1, no thermistor is connected to the operational amplifier 10.

As is indicated on the drawing, but merely for illustration of one workable circuit, the value of each of the resistors 5 and 6 is 330 ohms, of the resistor 16, 330 thousand ohms, and of the resistor 24, 20 thousand ohms. The capacitor 17 is rated at 1.0 microfarad, and the capacitor 25, at 4.7 microfarads. Both capacitors serve to smoothe the curve. The signal out terminals in the conventional circuit are electrically connected to an indicating device which displays a figure indicating percentage of breath alcohol as a function of the peak voltage generated by the fuel cell. In the present invention, the figure indicating percentage of breath alcohol is a function of the total area under the curve during a predetermined period between the beginning of the oxidation process and the return of the voltage to a substantially steady minimum state, as generated by the integrator 29.

In practicing the method of this invention on the device described, the device is first calibrated by using a standard, because every fuel cell is likely to have slightly different characteristics. The integral obtained must be divided by a factor so that the result displayed is the blood alcohol equivalent of the breath standard used. The various methods of calculating and applying this factor will be obvious to those skilled in the art. In the present example, the time to reach peak is measured by the device, multiplied by 12, and the integration terminated at the end of the time period thus calculated. Alternatively, the display in the present method could be triggered by the end of a predetermined time or on the reaching by the voltage of a substantially steady, but minimum state.

With either the standard or a breath sample, a base voltage is determined during the two or three seconds before the alcohol sample is taken into the fuel cell. This technique is conventional. The area under the curve as shown in FIG. 2 is then integrated over a period of time long enough to ensure that the voltage has dropped to a substantially constant minimum level. The area attributable to the base voltage is electronically subtracted from the total area. A somewhat more sophisticated method involves measuring the background at the beginning and end of the integration period and using an average of the two readings in the subtraction process. The measuring time will largely be determined by the value of the resistor 4. In the illustrative embodiment shown, it will be less than 75 seconds. It is unnecessary to short the terminals of the fuel cell, and a second test can be run immediately. The measuring time is preferably on the order of 8 to 15 times the length of time required for the voltage to peak.

It can be seen that, once calibrated, the device will give an accurate measure of the total alcohol content of the sample regardless of the initial height of the peak or the shape of the curve, so long as it reaches the substantially steady minimum state. Accordingly, variations in peak height as a result of repeated use or degradation of the fuel cell or as a result of different temperatures will have no affect upon the accuracy of the alcohol determination. In practice, with degradation of the cell over time, the effect is to lengthen the time within which the measurement is to be taken. If a measurement time of 90 seconds, for example, is taken as the longest practical time limit in field use, then the cell can be used for a long time without being replaced. If there is any question of calibration, the device can be tested against an alcohol standard.

As is suggested by FIG. 3, in the absence of shorting, the cell requires 10 or 15 minutes to tail off. Even with the shorting process, the tailing off requires about 150 seconds, and the problem of the variations in the height of the peak, which is conventionally what is measured, remains.

Numerous variations in the construction of the apparatus and the practice of the method of this invention, within the scope of the appended claims, will occur to those skilled in the art in the light of the foregoing disclosure. Merely by way of illustration and not of limitation, the resistance of the resistor between the fuel cell output terminals can be increased or decreased somewhat from the value shown but will always be low as compared with the conventional fuel cell breath analyzer, in which the external resistance between the terminals is between 300 and 1,000 ohms. The time in which the measurement is to be taken can be varied and will be varied with the amount of resistance across the fuel cell output terminals and with different characteristics of specific fuel cells. The current output of the cell may be measured directly without recourse to an external resistor by connecting the negative terminal of the fuel cell to the inverting input of an operational amplifier. This configuration results in the fastest possible response, since the electrons are detected as quickly as they are produced by the oxidation of the alcohol, and as voltage is allowed to build up across the terminals of the detector. The reading of the detector can be triggered by the reaching of the substantially steady minimum voltage, by a comparator system. The integration can be performed in alternate ways, such as using the amplifier output to charge a capacitor and terminating the integration when the voltage on the capacitor reaches a steady maximum state, said maximum voltage then being the measure of the integral. As has been suggested by the fact that the measurement can be terminated after a given time period has elapsed, the measurement can be terminated before the curve has actually returned to the base line, and the area extrapolated to what it would have been had the measurement been continued past that point. Such mathematical manipulation of the curve is simply an alternative method of practicing the teaching of the present invention. Other methods of integration will be apparent to those skilled in the art.

Having thus described the invention, what is claimed and desired to be secured by Letters Patent is:

1. The method of measuring breath alcohol concentration in which a breath sample is introduced to a fuel cell, and means are provided for measuring the flow of electrons from said fuel cell resulting from oxidation of said breath alcohol, said flow rate rising to a peak and thereafter falling to a substantially steady minimum base to form a curve, comprising integrating the entire area under the curve in the period between the beginning of oxidation and the reaching by the voltage of said substantially level minimum, and generating an intelligible signal representing alcohol content of the breath sample as a function of said area.

2. The method of claim 1 including the step of establishing a base line output voltage of said cell immediately before oxidation of alcohol begins, and electronically subtracting the area representing that voltage over the output voltage measuring time during the oxidation process from the area under the voltage curve during said measuring time.

3. The method of claim 1 wherein the measuring period is on the order of 8 to 15 times the length of time between the beginning of oxidation and the reaching of a peak voltage.

4. In apparatus for measuring breath alcohol content by oxydizing breath alcohol in a fuel cell having output terminals across which a voltage is generated, said voltage rising in response to the presence of alcohol in a breath sample in contact with said fuel cell and falling again to a base level, to establish a voltage time curve, the improvement comprising means for integrating the entire area under said curve from the inception of the rise in voltage to its reaching of said base level, and means for displaying a number indicating breath alcohol content as a function of said area.

* * * * *